US00PP11591P

United States Patent [19]

Baugher

[11] Patent Number: Plant 11,591

[45] Date of Patent: Oct. 24, 2000

[54] PEACH TREE NAMED 'R1-T2'

[75] Inventor: Phillip D. Baugher, Asper, Pa.

[73] Assignee: Adams County Nursery, Inc., Aspers, Pa.

[21] Appl. No.: 09/218,296

[22] Filed: Dec. 22, 1998

[51] Int. Cl.[7] ..... A01H 5/00

[52] U.S. Cl. ..... Plt./198

[58] Field of Search ..... Plt./198

[56] References Cited

U.S. PATENT DOCUMENTS

P.P. 5,503 7/1985 Weinberger ..... Plt./198

P.P. 8,169 3/1993 Friday ..... Plt./198

*Primary Examiner*—Howard J. Locker
*Assistant Examiner*—Melissa L. Kimball
*Attorney, Agent, or Firm*—James A. Lucas A. Lucas; Driggs, Lucas, Brubaker & Hogg Co., L.P.A.

[57] ABSTRACT

A new and distinct variety of peach tree, designated 'R1-T2', originated as a seedling in a block of 'John Boy'. It is a midseason variety maturing 5 to 7 days after 'John Boy' and 5 to 7 days before 'Loring'. The fruit is yellow-fleshed, freestone, large sized, and flavorful. The surface of the fruit is 70 to 80% attractive orange-red over a yellow-orange background.

3 Drawing Sheets

BACKGROUND OF THE DISCLOSURE

This invention relates to peach trees and, more specifically, to peach trees referred to as a variety of *Prunus persica* Batsch.

I discovered this new and unique variety of peach tree as a seedling growing in a row of 'John Boy' (U.S. Plant Pat. No. 6,827) in a cultivated area near Aspers, Pa. The tree of this invention produces a fruit of attractive commercial value, ripening after 'John Boy' and before 'Loring'(unpatented).

This new variety of peach was asexually reproduced by grafting near Aspers, Pa. and such reproduction has shown this new variety to come true in two successive generations. This propagation of the new variety by grafting under standard controlled conditions clearly discloses the continued maintenance of the characteristics described herein which distinguish this new variety from the parent variety and other related varieties of peach trees.

SUMMARY OF THE INVENTION

This new and distinctive variety of peach tree produces a yellow-fleshed, freestone fruit that is attractively colored, large, firm and flavorful. It ripens prior to 'Loring' and after 'John Boy', two midseason varieties grown in the Mid-Atlantic region. The fruit has a full red blush that is more attractive than 'Loring' and similar to 'John Boy'. The tree is vigorous and has a regular bearing habit.

DESCRIPTION OF THE DRAWINGS

This new variety of peach tree is illustrated by the accompanying photographic drawings and depicts the plant by the best possible color representation using color photography.

BOTANICAL DESCRIPTION OF THE PLANT

Figure 1:
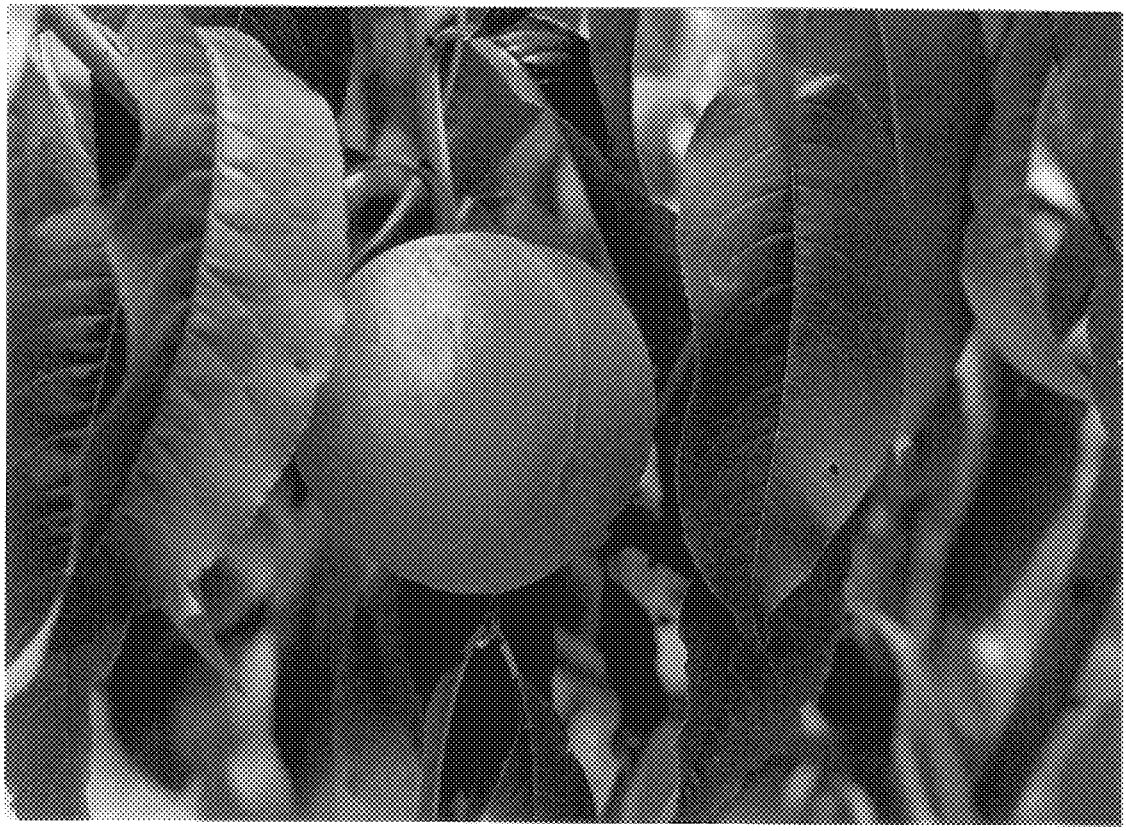
FIG. 1 is a close-up which depicts one specimen of fruit of the new tree, reflecting the characteristic shape, size and red blushed skin color over a contrasting yellow ground color. Also shown is the pistil point and suture of the fruit of this new tree.
Figure 2:
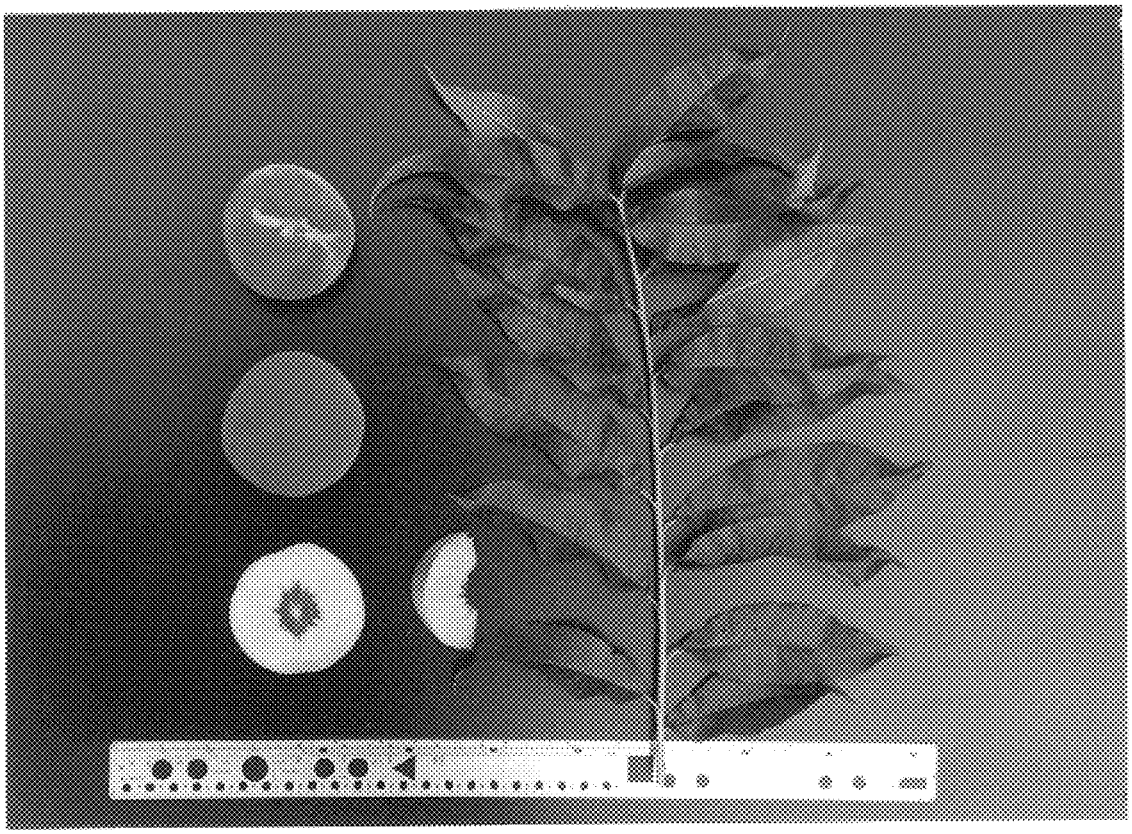
FIG. 2 depicts, at the top left, a whole specimen of the fruit shown from the stem end; at the middle left, a whole specimen of fruit from the apex; on the bottom left, a partially dissected fruit; on the right, a branch showing current season's growth, leaves, leaf arrangement and leaf spacing; and below, a ruler to reflect the scale of the plant parts.
Figure 3:
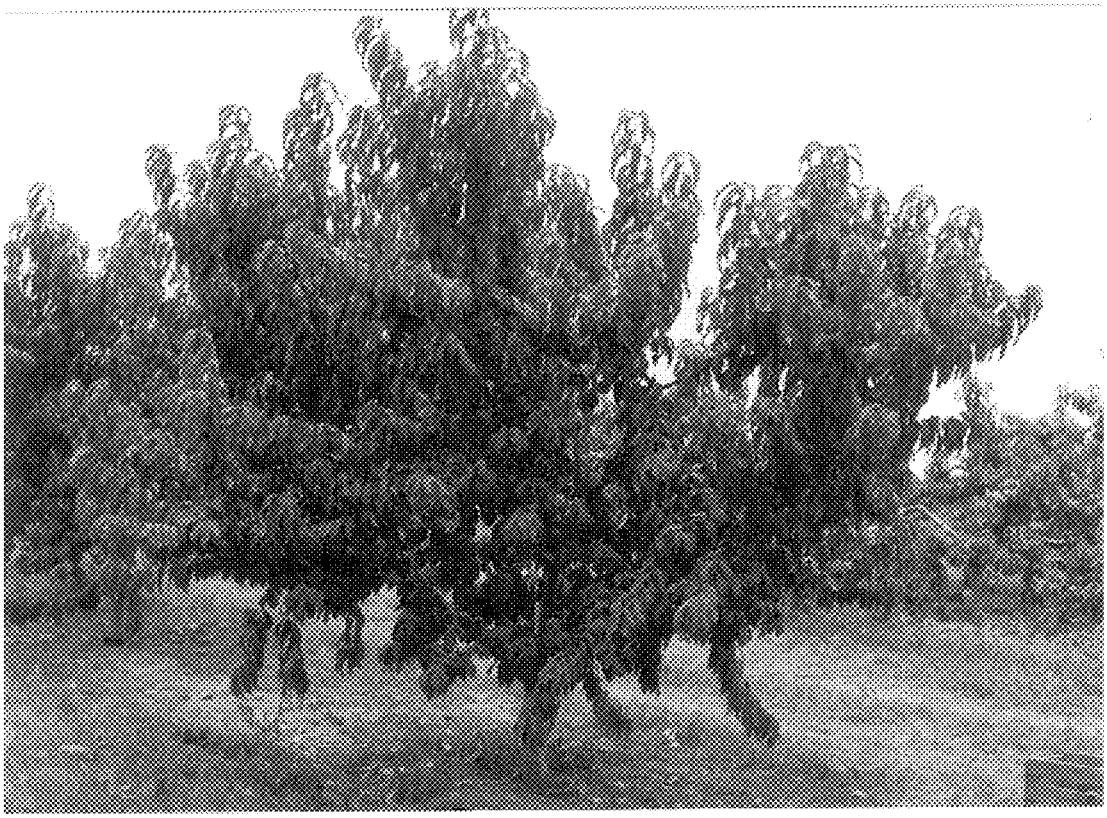
FIG. 3 shows a second generation, 4-year-old tree, illustrating typical tree form and productivity.

All color references below are measured against The Royal Horticultural Society Colour Chart. Colors are approximate as color depends on horticultural practices such as light level and fertilization rate, among others.

Parentage: Seedling of *Prunus persica* and 'John Boy' (U.S. Plant Pat. No. 6,827), pollen parent unknown. Asexually reproduced by bud grafting.

Tree:

- *Height and width* (*4-year-old tree grown on Lovell rootstock, Aspers, Pa.*).—8 feet by 12 . Large size, vigorous.
- *Terminal shoot length.*—16 to 20 inches.
- *Canopy.*—Open, upright-spreading, vase tree form 45 degree branch angle at juncture with trunk.
- *Bearing.*—Medium productive, 1½ bushels per tree in 5th leaf, annual bearer, half hardy, sensitivity to freeze damage similar to 'Loring'.
- *Trunk.*—Medium girth, 3½ inch diameter at 8 inch height from ground, medium smooth.

Branches: Medium girth, medium smooth, reddish gray, medium glossy.

Lenticels: Medium number, medium-small.

Leaves:

- *Length.*—6½ to 7 inches.
- Width.—1¾ to 2¼ inches. Medium sized, lanceolate, pointed, thin smooth.
- *Color.*—Olive green, R.H.S. 137A (from The Royal Horticultural Society Colour Chart) on top surface, R.H.S. 137C on bottom surface.
- *Margins.*—Serrate.
- *Petioles.*—Short — ⅜ inch, medium thick.
- *Glands of petioles.*—0 to 4, opposite, mostly globose, some reniform, green.

Flowers:

*Dates of first and full blossoms.*—Average April 19 and April 23 (compared to April 21 and 25 for 'Redhaven' (unpatented)) in Aspers, Pa.

*Flowering*—Mid-season, blooms with 'Loring'.

*Pollination requirements.*—Self-fertile.

*Size.*—Medium, showy.

*Bloom density.*—Medium.

*Color.*—Rich pink, R.H.S. 65B.

Fruit:

*Dates of first and last pickings.*—Average August 13 and 19 (compared to August 7 and 12 for 'John Boy'; August 19 and 25 for 'Loring') in Aspers, Pa.

*Days from peak bloom to "harvest ripe" stage.*—115.

*Number of pickings.*—3.

*Maturity when described.*—Firm-ripe.

*Size.*—Uniform, medium-large (similar to 'John Boy' and 'Loring').

*Shape and dimensions of fruit—Axial diameter.*—2½ to 2¾ inches.

*Transverse in suture plane.*—8¾ to 9 inches circumference.

*At right angles to suture plane.*—8¾ to 9 inches circumference.

*Form.*—Variable, globose to slightly oblong, symmetrical.

*Suture.*—An inconspicuous line, continuous from stem end to apex, has slight marked depression at pistil point, generally not raised.

*Ventral surface.*—Rounded, lips equal.

*Cavity.*—Rounded, suture showing on one side, depth ½ inch, breadth ⅝ inch, no markings.

*Base.*—Rounded.

*Apex.*—Rounded to truncate.

*Stem.*—Short length, glabrous, medium adherence to stone.

*Skin.*—Medium thick, medium tender, free, no tendency to break.

*Color.*—Highly blushed deep orange-red, R.H.S. 46A, covering 70 to 80% of fruit surface (compared to 30 to 40% with 'Loring'), over yellow-orange background, R.H.S. 22C. Mostly even with a few stripes or blotches.

*Down.*—Moderate, short.

*Flesh.*—Yellow color, R.H.S. 10C, occasional red streaks, slow rate of oxidation.

*Surface of pit cavity.*—Red, R.H.S. 46A.

*Texture.*—Firm, ~6 lbs at harvest.

*Fibres.*—Few, fine.

*Ripens.*—Fairly evenly.

*Flavor.*—Delicate, sweet, ~13% soluble solids.

*Aroma.*—Mild.

*Eating quality.*—Good to best.

*Stone.*—Free.

*Color.*—Red, R.H.S. 46A.

*Fibres.*—Part from flesh smoothly.

*Size.*—Medium.

*Length.*—1¼ inch.

*Thickness.*—1 inch.

*Form.*—Oblong.

*Base.*—Oblique.

*Hilum.*—Narrow.

*Apex.*—Acute.

*Sides.*—Equal.

*Surface of stone.*—Furrowed throughout, moderate number of pits.

*Ridges.*—Rounded toward apex.

*Pits.*—Circular or elongated.

Uses: Local, dessert and culinary markets. Flesh resists browning, making it ideal for canning and freezing.

Keeping quality: Excellent.

Resistance to insects: Medium.

Resistance to diseases: Medium, no bacterial spot.

Shipping quality: Good to excellent.

I claim:

1. A new and distinct variety of peach tree, as illustrated and described, characterized by fruit of 70 to 80% attractive orange-red color over a yellow-orange background, large size and firm, non-browning flesh.

* * * * *